United States Patent [19]

Vincent et al.

[11] Patent Number: 5,197,088
[45] Date of Patent: Mar. 23, 1993

[54] ELECTRON BEAM X-RAY COMPUTER TOMOGRAPHY SCANNER

[75] Inventors: Paul Vincent, Karlsruhe; Günther Laukien, Rheinstetten, both of Fed. Rep. of Germany

[73] Assignee: Bruker Analytic, Fed. Rep. of Germany

[21] Appl. No.: 695,578

[22] Filed: May 3, 1991

[51] Int. Cl.⁵ .............................................. H05G 1/60
[52] U.S. Cl. ...................................... 378/10; 378/137
[58] Field of Search ............................. 378/4, 10, 137

[56] References Cited

U.S. PATENT DOCUMENTS

| | | |
|---|---|---|
| 4,158,142 | 6/1979 | Haimson . |
| 4,300,051 | 11/1981 | Little ................................ 378/10 |
| 4,352,021 | 9/1982 | Boyd et al. . |
| 4,521,900 | 6/1985 | Rand . |
| 4,521,901 | 6/1985 | Rand . |

FOREIGN PATENT DOCUMENTS

2640455 of 0000 Fed. Rep. of Germany .
8390478.6 of 0000 Fed. Rep. of Germany .
61-68032 8/1986 Japan .

*Primary Examiner*—Craig E. Church
*Attorney, Agent, or Firm*—Wolf, Greenfield & Sacks

[57] ABSTRACT

An electron beam x-ray computer tomography scanner is improved so that a compact, tiltable configuration without mechanical motion is achieved. By introducing the electron beam in a direction which is largely parallel rather than perpendicular to the scan plane, the long large diameter evacuated electron beam pipe of prior art is eliminated. As a result, the scan system according to the invention enjoys compact dimensions compared to those of prior art, and free access to the scan region from both the front and back of the scanner is possible.

16 Claims, 10 Drawing Sheets

ELECTRON BEAM X-RAY COMPUTER TOMOGRAPHY SCANNER

FIELD OF THE INVENTION

The invention concerns an electron beam x-ray computer tomography scanner which is compact in size, tiltable, and in which neither the x-ray source nor the x-ray detector are caused to rotate while scanning.

DESCRIPTION OF THE PRIOR ART

Electron beam x-ray computer tomographs without mechanical motion of the x-ray source or the detectors are known in the art from U.S. Pat. Nos. 4,352,021 and 4,158,142. Further improvements of the system described in U.S. Pat. No. 4,352,021 are described in U.S. Pat. No. 4,521,900 and U.S. Pat. No. 4,521,901.

In conventional computer tomographs, the x-ray source and/or the detector arrangement are mechanically moved around an object. These tomographs are usually limited to scan times of about 1 second for a complete 360 degree scan. When mechanical motion is not necessary, significantly shorter measurement times are possible, that is to say, faster scans which can be utilized for the study of quickly moving objects such as the human heart.

In U.S. Pat. Nos. 4,352,02 and 4,158,142, the moving x-ray source is replaced with an electron beam which collides with an arc-shaped anode from a direction which is largely perpendicular to the scan-slice. U.S. Pat. No. 4,352,021 describes a method whereby two dipole magnets guide the electron beam in such a way that its focus approximately describes an arc of 210 degrees over the anode surface. The x-ray radiation which is emitted from the anode is detected by means of an arc-shaped detector arrangement, situated across from the anode and likewise describing an arc of approximately 210 degrees. Thereby, neither the anode nor the detector arrangement describe a full circle and there is only a relatively small overlap region. The described preferred embodiment does not use one but four anode rings (in the following "ring" also represents a ring segment), the four rings each being slightly displaced with respect to each other in a direction largely perpendicular to the scan slice. By successively guiding the electron beam along each of the four anodes and by measuring, with each anode scan in each of the adjacent detector arcs, the x-ray radiation passing through the object, one obtains data sets which are sufficient for the reconstruction of a total of eight largely adjacent slice images from the object.

In U.S. Pat. No. 4,158,142, the relative geometric arrangement of the electron and x-ray sources is similar to that in U.S. Pat. No. 4,352,021. There are, however, differences with regard to the electromagnetic guiding and focussing of the electron beam and there is a complete 360 degree encompassing anode ring and a complete 360 degree encompassing detector ring. The detector and anode rings are coaxial but not coplanar.

The configurations of the U.S. Pat. No. 4,352,021 and 4,158,142 utilize long evacuated electron beam pipes in order to introduce the electron beam onto the anode, which in turn leads to a substantially larger space requirement than that which is usually associated with tomographs utilizing mechanical motion. Moreover, the connection between the electron beam pipe and the anode region and, thereby, their associated integration into the gantry prevents tilting of the gantry unit in order to change the orientation of the scan slice through the object. In addition, the presence of the large funnel-shaped electron beam pipe behind the anode region interferes with the horizontal travel of the object support system (in general the patient bed) and access to the object being scanned is also reduced. Moreover, the enclosed tunnel-like shape of the electron beam pipe results in patient discomfort and claustrophobia. The use of a partial scan of only 210° as described in U.S. Pat. No. 4,352,021 is associated with reduced image quality compared to that of conventional scanners with mechanical motion.

Further disadvantages of the non-mechanical computer tomography scanners of prior art are associated with the use of ion aided focussing to help focus the electron beam at the anode. Small focal spot sizes are required for good high contrast resolution and good system frequency band pass, i.e. good image quality. In the computer tomography system described in U.S. Pat. No. 4,352,021, 4,521,900, and 4,521,901, the size of the focal spot is inversely related to the size of the electron beam at the location of the focussing magnets, i.e. the electron beam must first expand in order for it to be effectively focussed onto the anode. However, the natural occurrence of ion aided focussing between the electron beam source and the magnetic focussing elements inhibits the electron beam from expanding to the required radius. Therefore, ion aided focussing is required between the focussing magnets and the anode, but must be eliminated between the electron beam source and the focussing magnets. For this reason, the systems according to prior art require the installation of ion traps to sweep the positive ions away from the electron beam in the region between the electron beam source and the focussing magnets. These ion trap electrodes represent an additional design complication and are associated with significant additional expense.

Because of the above mentioned deficiencies in electron beam x-ray computer tomography systems without mechanical motion of the x-ray source or x-ray detector, it is the purpose of the present invention to further improve an electron beam x-ray computer tomography scanner for the production of image slices through an object, with an electron beam source as well as electron beam guiding means, with a stationary anode and an x-ray detector ring, wherein the electrons from the electron beam source form an electron beam which collides with the anode ring at a focal spot which, for its part, emits x-ray radiation, in such a way that there is free access to both sides of the scan region, that the space requirements need not be larger than those for conventional scanners with mechanical motion, and that it is possible to tilt the gantry to change the orientation of the scan slice through the object.

BRIEF SUMMARY OF THE INVENTION

The purpose of the invention is achieved by guiding the electron beam from the electron beam source into collision with the anode along a path which is largely parallel to the plane of the anode.

In this manner, the purpose of the invention is completely accomplished. By guiding the electron beam in a direction which is largely parallel rather than perpendicular to the scan plane, the long large diameter evacuated electron beam pipe of prior art is eliminated. As a result, the scan system according to the invention enjoys compact dimensions compared to those of prior art, and free access to the scan region from both the front and back of the scanner is possible. Furthermore, the complications associated with joining the long evacuated electron beam pipe of prior art in a vacuum sealing fashion onto the anode and scan region which prohibited tilting of the gantry are eliminated. As a consequence, the gantry can be easily tilted to angles comparable to those achieved in conventional scanners with mechanical motion, i.e. to +/−25° from the vertical.

By guiding the electron beam around the anode region using electron beam guiding means, the electron beam envelope is caused to describe an arc which is largely coplanar with the anode, and the large, long, cumbersome conical electron beam envelope and associated conical electron beam pipe oriented perpendicular to the scan plane are eliminated. The electron beam guiding means cause the electron beam to come into collision with the anode in such a way that essentially full 360° scans are allowed.

In a preferred embodiment of the invention, the electron beam source exhibits an electron gun for the generation of the electron beam.

This measure has the advantage that electron guns are compact in size and capable of producing large currents with good electron beam quality.

The compact nature of the electron gun allows the amount of space which is needed for generation of the electron beam to be kept to a minimum thereby reducing the overall size of the apparatus according to the invention. Furthermore, its large current capability and good beam quality are important for good image quality. In particular, for fast scans in which, for example, the entire largely 360° scan is effected in tens of milliseconds, image quality is strongly influenced by the integrated detected x-ray flux. This is due to the fact that the image quality depends on the signal to noise level of the detected signals which is, in turn, determined by the incoherent addition of fluctuations due to photon statistics with uncertainties due to electronic and other sources of noise (noise floor). For fast scans, the signals are small and the noise floor limits image quality. Since the x-ray yield is directly proportional to the amount of electron current, it is particularly advantageous, in fast scans, to have as much electron current available as possible. Modern electron guns are, by way of example, capable of producing ampere of 130 kV electrons.

Good electron beam quality is an additional important feature for image quality. In particular, the area and shape of the region of intersection between the electron beam and the anode, i.e. the focal spot, must be small in order to effect good high contrast resolution and broad frequency response for imaging. The low emittance and small cathode sizes of electron guns allow for small, by way of example, 1–3 mm diameter focal spot sizes to be achieved.

In a further preferred embodiment of the invention, there are a plurality of electron beam sources.

This measure has the advantage that the maximum path length traveled by the electron beam is reduced by a factor roughly equal to the number of sources used and, as a result of said reduced maximum path length, problems associated with electron beam divergence and focussing are greatly reduced.

In a further preferred embodiment of the invention, the electron beam source is positioned in such a way that the electron beam is initially injected, over a short distance, largely perpendicular to the direction of the circulating electron beam before being bent into the direction of the circulating electron beam using injection means exhibited by the electron beam source.

This measure has the advantage, that the space required for the electron beam source, i.e. electron gun, can be taken from a region which is somewhat removed from the anode, thereby facilitating electron beam generation with a minimum amount of interference with those portions of the anode, x-ray detector, and electron beam guiding means located in close proximity to the electron beam source, which, in turn, allows easier realization of essentially complete 360° scans.

In a preferred variation of this embodiment, the injection means exhibit means to deflect the electron beam into either clockwise or counter-clockwise orbit about the object being scanned.

This variation of the present embodiment has the advantage that the maximum distance which needs to be traveled by the electron beam is approximately halved resulting in substantially simpler electron beam focussing and steering requirements.

In another preferred variation of this embodiment of the invention, the injection means exhibit an electric field.

This variation has the advantage that a simple injection system can be realized with minimum interference with the injecting electron beam. By way of example, the electric field can be in the form of an electrostatic mirror and made from a highly transparent wire mesh. Such a mirror system could be inserted directly into the path of the electron beam such that, without voltage applied to it, the electron beam would pass largely unaffected through the grid. Such a system allows for increased flexibility in the design of the injection means and electron beam guiding means since the transparent electrostatic mirror can be effectively introduced into or removed from the electron beam focussing, guiding and injection optics in a time dependent fashion simply by regulating the applied voltage.

In a further preferred variation of this measure in accordance with the invention, the injection means exhibit a magnetic field.

This variation has the advantage that a stable injection system is realized without the need for high voltages to steer the electron beam into the scan plane. The magnetic fields can be realized through the use of electromagnets or permanent magnets.

In another preferred embodiment of the invention, the electron beam source is positioned largely in the scan plane, with the electron beam being directly injected along the direction of the circulating electron beam.

This measure has the advantage that the injection means is either eliminated or greatly simplified since there is no longer a need to bend the electron beam through an arc of, by way of example, 90°.

In a further preferred embodiment of the invention, the anode and x-ray detector are in the form of an anode ring and an x-ray detector ring with the radius of the anode ring being larger than that of the x-ray detector ring and the electron beam is guided along a path whose radius is larger than that of the x-ray detector ring and smaller than that of the anode ring.

This measure has the advantage that the x-ray fan beam originating at the focal spot need only pass through a minimum amount of x-ray beam attenuating material before entering the x-ray detector in addition to the material exhibited by the object being scanned. This measure also has the advantage that the geometry specified allows a simple and effective solution to the problems of electron beam transport and guidance into collision with the anode.

In a preferred variation of this embodiment, the x-ray detector and anode rings are largely coplanar, and the x-ray detector ring is split into two closely spaced x-ray detector partial rings of equal radius which are separated by a gap, said gap being large enough to allow x-rays emerging from the focal spot to pass through, but small enough to allow a large fraction of the x-rays transmitted through the object being scanned to be detected. This condition is fulfilled, by way of example, when the relationship Rd/Rf (wd−g)/(wd+g) is approximately satisfied where g is the width of the gap between the two x-ray detector half-rings, wd the width of the x-ray fan beam after penetration of the object being scanned at the location of the x-ray detector ring across from the focal spot, Rd the x-ray detector ring radius, and Rf the radius of the arc described by the focal spot around the anode ring.

This variation of the present embodiment according to the invention has the advantage that the scan slice has a more uniform thickness resulting in improved image quality and reduced partial volume artifacts.

In a further preferred embodiment of the invention, the electron beam guiding means exhibit electron beam steering and focussing means, and electron beam extracting means.

This measure has the advantage that the electron beam is guided from the electron beam source to the focal spot without significant losses in electron beam current, with said focal spot moving continuously around the anode in a predetermined fashion throughout the course of the scan, while maintaining a focal spot size which is sufficiently small for good image quality. The electron beam steering means keep the electron beam in a stable orbit as it travels from the electron beam source to the predetermined position on the anode at which the focal spot is to be located. The electron beam focussing means keep the electron beam from increasing to a size which would prohibit its transport from the electron beam source to the focal spot and maintain an adequately small focal spot size for good image quality. The electron beam extracting means remove the electron beam from its orbit into a collision with the anode at the predetermined focal spot location, said focal spot being moved continuously about the anode during the course of a complete scan.

In a further preferred embodiment of the invention, the electron beam guiding means exhibit ion aided focussing.

This measure has the advantage, particularly for large electron beam currents, that the electron beam and focal spot radii are reduced in a particularly simple and effective fashion since, according to the invention and in contrast to prior art, the electron beam is not required to initially expand before it can be properly focussed, and the need for ion traps is either eliminated or greatly reduced.

In another preferred embodiment of the invention, the electron beam guiding means exhibit magnetic fields.

This measure has the advantage that the required forces on the electron beam are easily achieved either using electromagnets or permanent magnets and, in the event of ion aided focussing, the massive slowly drifting focussing ions remain largely unaffected by said magnetic guiding means.

In another preferred embodiment of the invention, the electron beam guiding means exhibit electric fields.

This measure has the advantage that, by way of example, the required focussing and steering forces on the electron beam are easily achieved without requiring a large amount of material in or near the electron beam. In this connection, said electric fields can be generated using wire mesh electrodes which are essentially transparent to the electron beam when no relative voltage difference is applied.

This measure also has the advantage that, in the event of ion aided focussing, the force acting on both the electrons and the ions can be the same, independent of their greatly differing speeds, thereby providing additional flexibility in focussing, steering, and extracting the combined electron-ion system.

In another preferred embodiment of the invention, the electron beam guiding means exhibit both electric and magnetic fields.

This measure has the advantage that maximum flexibility in system design and adjustment is allowed since the differing advantageous features of both magnetic and electric fields outlined above can be utilized where said respective features are appropriate.

Further advantages can be derived from the description and the accompanying drawings. Clearly, the characterizing features mentioned above and described below are applicable not only in the corresponding combination given but also in other combinations or by themselves without departing from the framework of the current invention.

Embodiments of the invention are represented in the drawings and are described in the following description. Shown are.

BRIEF DESCRIPTION OF THE DRAWING

DETAILED DESCRIPTION OF THE PREFERRED EMBODIMENTS

Figure 1:
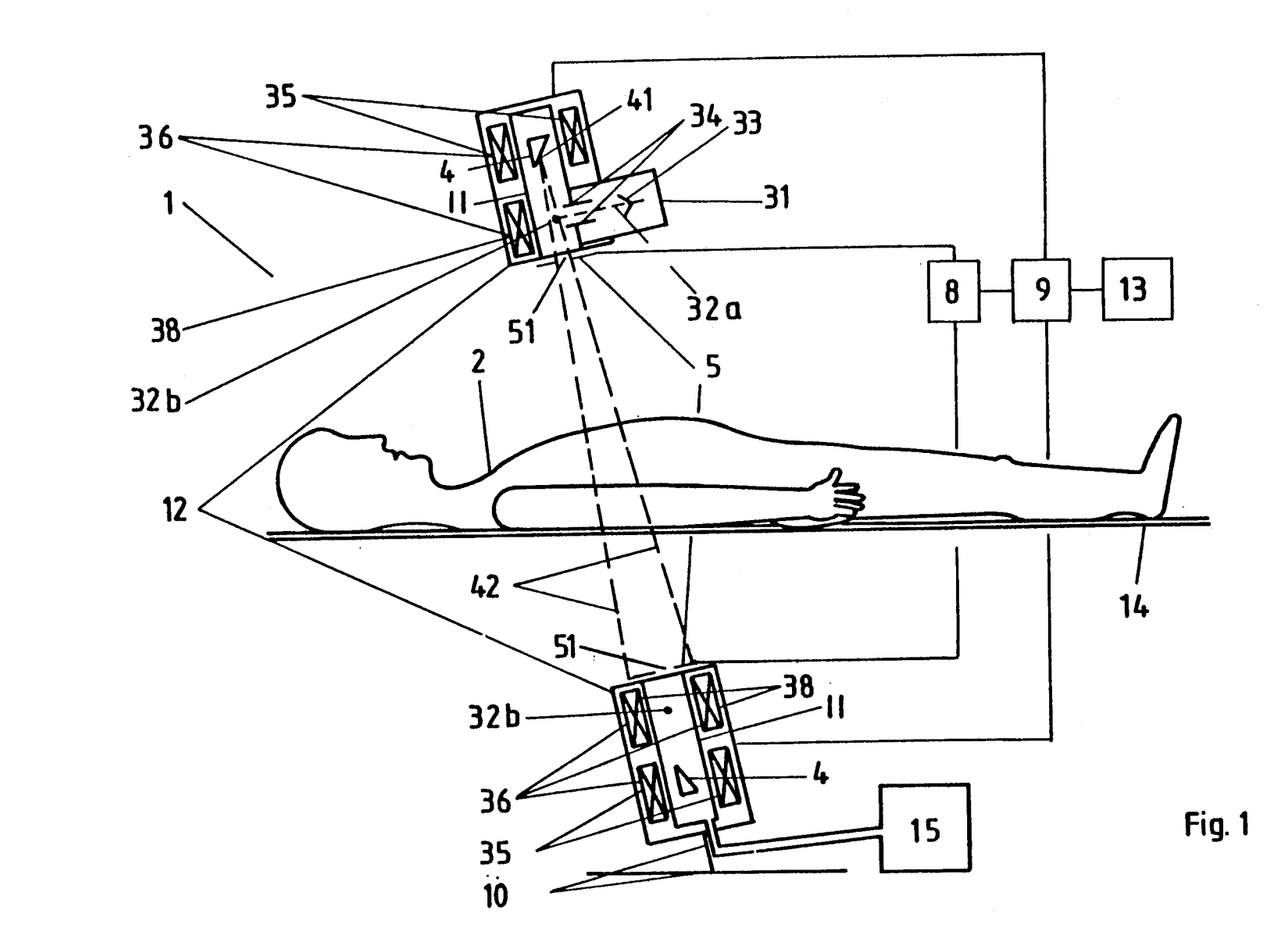
FIG. 1: Overview of an electron beam x-ray computer tomography scanner according to the invention.

FIG. 1 shows a cross section through a preferred embodiment of an electron beam x-ray computer tomography system (1) according to the invention. An electron beam source (31) introduces an electron beam (32a,32b) into the vacuum vessel (11). The electron beam source (31) exhibits an electron source (33) which can be in the form of an electron gun for the production of the electron beam (32a) and injection means (34) for guiding the injecting electron beam (32a) into the portion of the vacuum vessel designed for the circulating electron beam (32b). The electron beam (32b) is guided around the vacuum vessel (11) with electron beam guiding means (36). Electron beam guiding means (36) exhibit electron beam extracting means (35) to extract the circulating electron beam (32b) into a collision with the anode (4) at the focal spot (41), and electron beam steering and focussing means (38) to maintain the circulating electron beam (32b) along the desired path. As a consequence of the collision between the electron beam (32b) and the anode (4), the electrons in the electron beam (32b) are stopped and emit an x-ray fan beam (42). The x-ray fan beam (42) passes through the object (2) being scanned and the transmitted intensity is detected in an x-ray detector (5). Said object (2) is supported during the scan on an object support (14). The x-ray detector (5) exhibits a gap (51) which is large enough to allow the x-ray fan beam (42) emerging from the focal spot (41) to pass through the x-ray detector (5), but small enough to allow most of the x-ray intensity emerging from the object (2) to be detected in the portion of the x-ray detector (5) located across from the focal spot (41). Signals produced in the x-ray detector (5) are digitized by means of analog to digital converter (8) and passed to computer (9). The computer (9) reconstructs an image slice through the object (2) which can be displayed on screen (13). Computer (9) also controls and monitors the various scan functions of the x-ray computer tomography system (1). The orientation of the slice through the object cut by x-ray fan beam (42) can be adjusted through tilting of the gantry assembly (12) by means of tilt mechanism (10). A vacuum system (15) is connected to vacuum vessel (11) in order to measure, regulate, and change the pressure in vacuum vessel (11), depending on the desired conditions for ion aided focussing and scan operating conditions.

Figure 2:
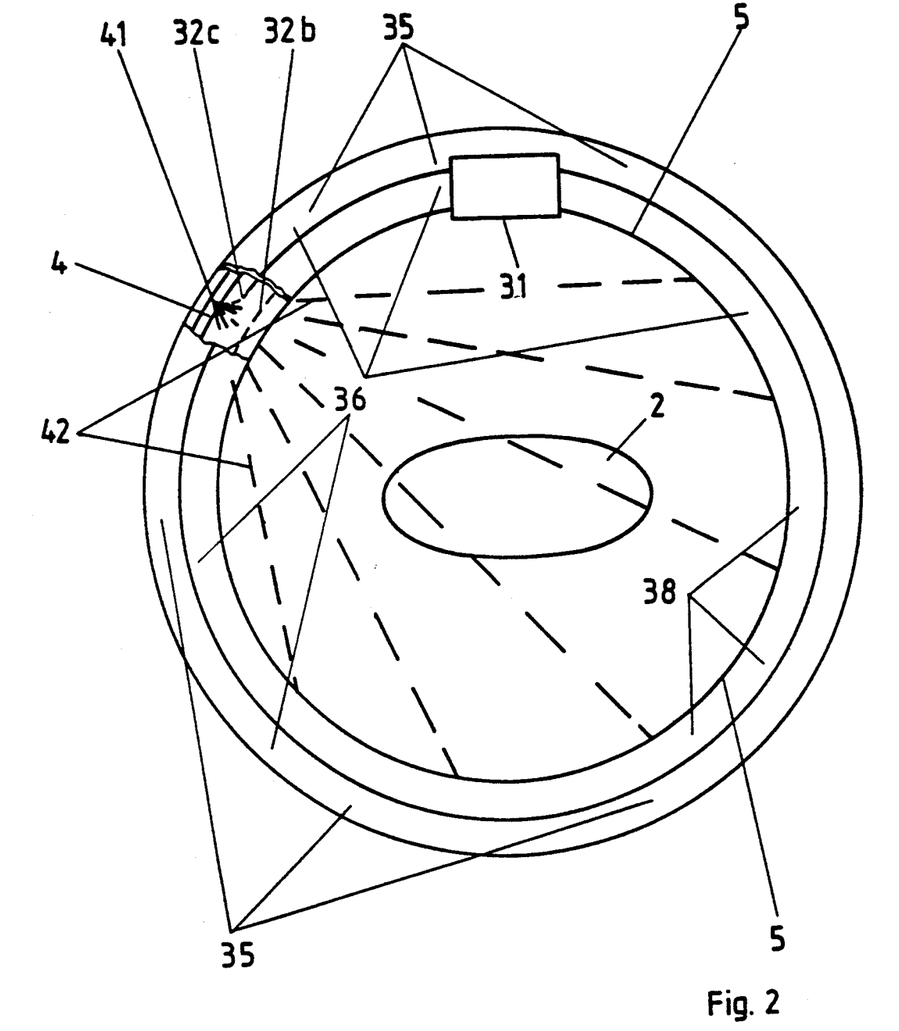
FIG. 2: Schematic front view of the scanner according to the invention.

FIG. 2 shows a front view of a preferred embodiment of the invention. The electron beam source (31) introduces the electron beam into the circulating electron beam (32b) region. Through adjustment of the electron beam guiding means (36), the circulating electron beam (32b) can be guided to become an extracted electron beam (32c) and caused to collide with the anode (4) at the focal spot (41) to produce the x-ray fan beam (42). The x-ray fan beam (42) is incident on the object (2) and the transmitted portion of the x-ray fan beam (42) is detected in the x-ray detector (5).

Figure 3:
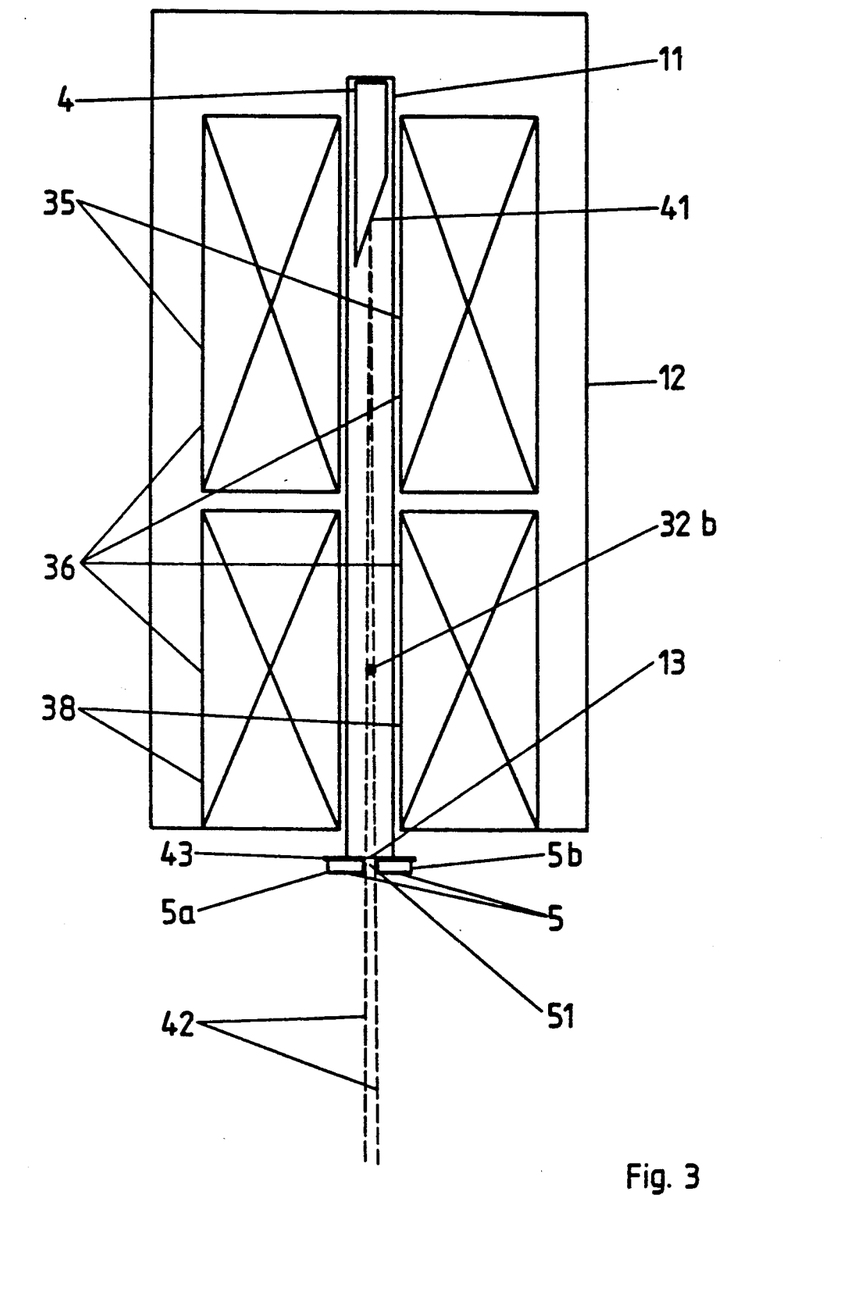
FIG. 3: Expanded cross sectional slice through the gantry.

FIG. 3 shows and expanded cross section of the gantry assembly (12) in a preferred embodiment of the invention. The geometry of the system is such that there is sufficient space to guide the circulating electron beam (32b) within the appropriate region of the vacuum vessel (11). Moreover, the x-ray detector (5) exhibits two half-detectors (5a,5b) which are separated by a gap (51) which is large enough to allow the x-ray fan beam (42) emerging from the focal spot (41) on the anode (4) to pass through, but small enough to detect most of the x-ray flux transmitted through to the opposite side of the x-ray detector (5) for detection. X-ray fan beam collimation (43) is provided for in order to define the width of the image slice through the object (2) and to prevent a large fraction of the x-rays emerging from the focal spot (41) from striking the x-ray detector (5) at the x-ray detector (5) location near the focal spot (41). The vacuum vessel (11) exhibits a vacuum window (13) to allow the x-ray fan beam (42) emerging from the focal spot (41) to exit the vacuum vessel (11) without significant attenuation. The vacuum vessel (11) contains the anode (4) and the electron beam (32) and allows for variable partial pressures which include, in particular, the range between $1 \times 10^{-7}$ to $1 \times 10^{-5}$ Torr. Electron beam guiding means (36) exhibit electron beam steering and focussing means (38) in the vicinity of the circulating electron beam (32b), and electron beam extracting means (35) in the vicinity of the anode (4).

Figure 4A:
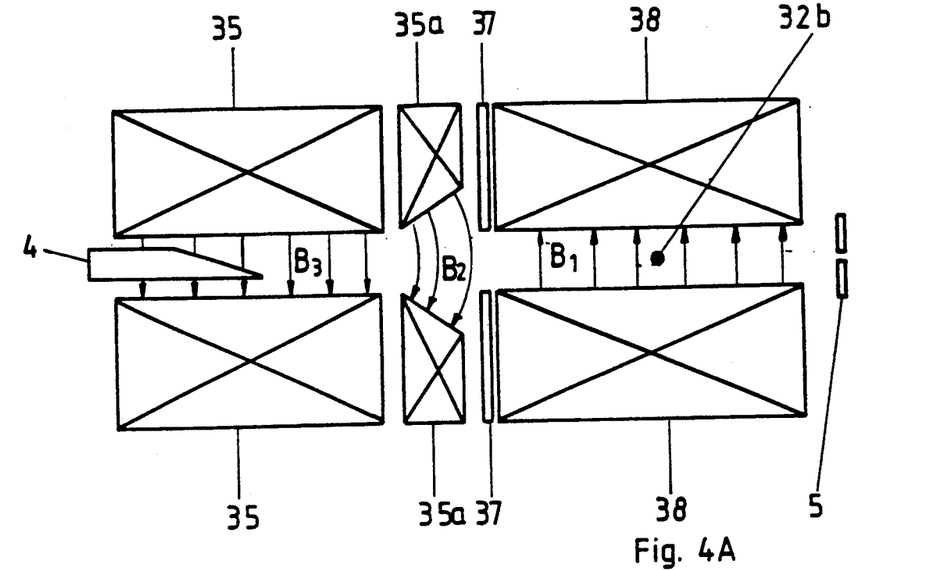
FIG. 4A: Possible scheme for electron beam extraction.

FIG. 4A represents a cross section of an embodiment of the invention in the region between the anode (4) and the x-ray detector (5) in which electron beam steering and focussing means (38) are used to generate a magnetic field $B_1$ in the region of the circulating electron beam (32b) and electron beam extracting means (35) also exhibit electron beam extracting and focussing means (35a) generating magnetic fields $B_3$ in the vicinity of the anode (4) and $B_2$ in the region between $B_1$ and $B_3$. Field clamp (37) helps to keep fields $B_3$ and $B_2$ from extending too far into the region of $B_1$. The direction of the magnetic fields $B_1$, $B_2$, and $B_3$ is schematically indicated by the arrows in FIG. 4A.

Figure 4B:
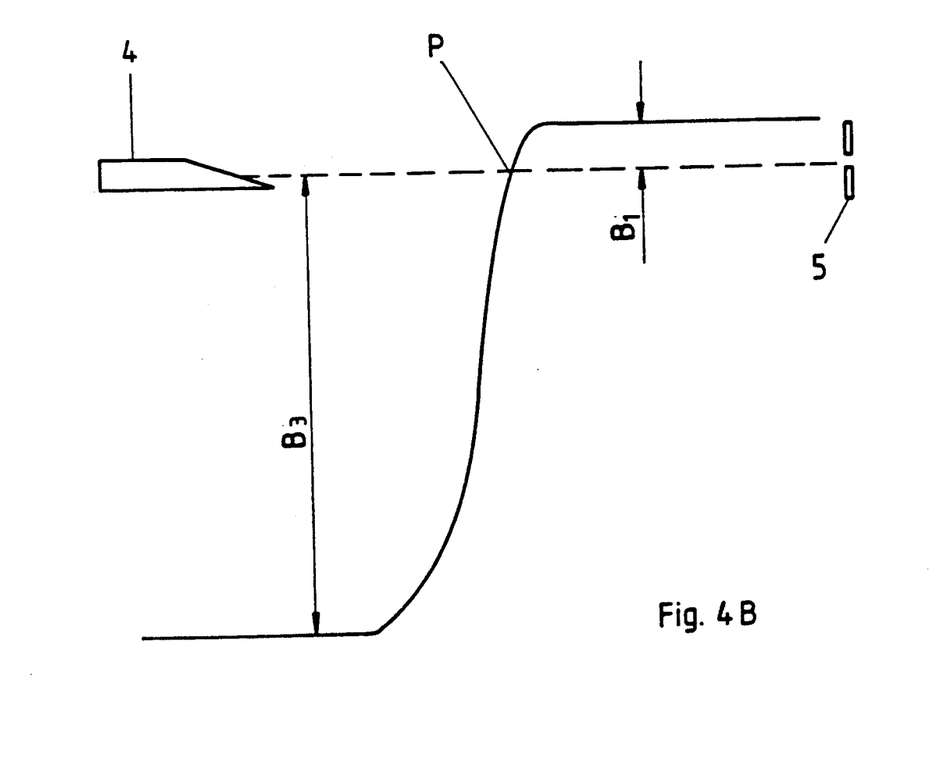
FIG. 4B: Magnetic field configuration in possible scheme for electron beam extraction.

In FIG. 4B, the magnitude of the magnetic fields in a direction largely transverse to the plane of the circulating electron beam (32b) as a function of the relative location between the x-ray detector (5) and the anode (4) is qualitatively indicated. $B_1$ and $B_3$ are of opposite sign and $B_3$ is much larger than $B_1$. There is a point P intermediate between $B_1$ and $B_3$ where the field is approximately zero.

In this schematic and simplified example of an embodiment of the invention, the extraction process can be envisioned as occurring between two oppositely directed magnetic fields $B_1$ and $B_3$. The $B_1$ field directs the circulating electron beam (32b) along the desired path. Extraction occurs when the $B_1$ fields in the appropriate locations are reduced in strength so that the circulating electron beam (32b) moves radially outward towards the anode (4). After reaching the point P, the electron beam enters the region of fields $B_3$ and $B_2$. Being large and of opposite sign to field $B_1$, field $B_3$ causes the electron beam to sharply deflect into collision with anode (4).

By way of example, for a 130 keV, 1 Ampere electron beam (32b), $B_1$ could exhibit magnetic field strengths for the purpose of steering the electron beam, which are largely dipole in nature with strengths of 20 gauss. For the purpose of focussing, $B_1$ could exhibit fields which are largely quadrupole in nature and with strengths of 5 gauss. The $B_3$ fields generated by electron beam extracting means (35) could be approximately 250 gauss.

Clearly gantry (12) can incorporate magnetic shielding to shield the electron beam (32b) from the effects of the earth's magnetic field, or the influence of the earth's field can be taken into account in determining the values of $B_1$, $B_2$, and $B_3$.

FIGS. 5A through 6B give examples of the dependence of the electron beam radius on space charge effects, with and without ion aided focussing. As the electron beam propagates along its path, it expands radially due to its initial divergence, i.e. emittance, its mutual electrostatic repulsion, and due to multiple scattering with residual gas along its path. The electromagnetic self interaction of the electron beam has two terms, an electrostatic repulsion term, and an attractive magnetic term. In the absence of ion aided focussing, the repulsive term is larger than the attractive term and the electron beam expands under the action of self-forces. However, in consequence of the scattering of the electron beam from residual gas along its path, a certain number of gas atoms become positively ionized and are drawn into the negatively charged electron beam, thereby causing its partial neutralization. As a result of this neutralization, the electrostatic repulsive term is reduced. Under certain conditions, the magnetic attraction term can be larger than the reduced electrostatic term, and the beam spontaneously focuses, hence the name ion aided focussing.

The advantages of ion aided focussing according to the invention, and the relationship among space charge expansion of the beam, i.e. the mutual electrostatic repulsion of the electrons in the beam, beam emittance, and ion aided focussing can be best illustrated with the aid of a simple model of the beam envelope. For a uniform cylindrically symmetric beam, the equation of the beam envelope radius r has been given by E. P. Lee and R. K. Cooper, Particle Accelerators 7, 83, 1976 and by J. D. Lawson, "Space Charge Optics", *Applied Charged Particle Optics*, edited by A. Septier, Academic Press, London, 1983, and U.S. Pat. No. 4,521,901. We have:

$$r'' = \epsilon^2/r^3 + K/r + gz/3r_o \qquad 1.$$

where z is the longitudinal distance traveled by the beam, r the radius of the beam envelope, $\epsilon$ the beam emittance, K the generalized beam perveance, $r_o$ the initial radius of the beam, and g a factor characterizing multiple scattering. r'' represents the second derivative of r with respect to z.

Equation 1 describes the radial acceleration of the beam with respect to distance traveled, z. The first term on the right hand side of the equation represents the expansion of the beam due to its finite emittance. The second term represents the effect of space charge on the beam, and the third term is the multiple scattering expansion of the beam due to the residual vacuum along the transport path. We also have:

$$K = 2Nr_c(1-\beta^2-f)/(\beta^2\Gamma) \qquad 2.$$

with N the number of electrons per unit length in the laboratory frame, $r_c$ the classical radius of the electron, $\beta$ is the ratio of the electron speed to the speed of light, $\Gamma$ the ratio of the relativistic mass of the electron to its rest mass, and f the neutralization fraction of the beam. If there are as many positive ions as electrons in the beam, $f=1$, the beam is neutralized, and K is negative, i.e. attractive. If there are no positive ions in the beam, $f=0$ and K is positive.

The factor g has a value which is directly proportional to the pressure along the electron beam path. In perfect vacuum, $g=0$. At a pressure of $1 \times 10^{-6}$ Torr, g is approximately $2 \times 10^{-10}$ cm$^{-1}$. It turns out that this term is usually small compared to the first and second terms and can normally be neglected in the cases of interest to us here.

Figure 5A:
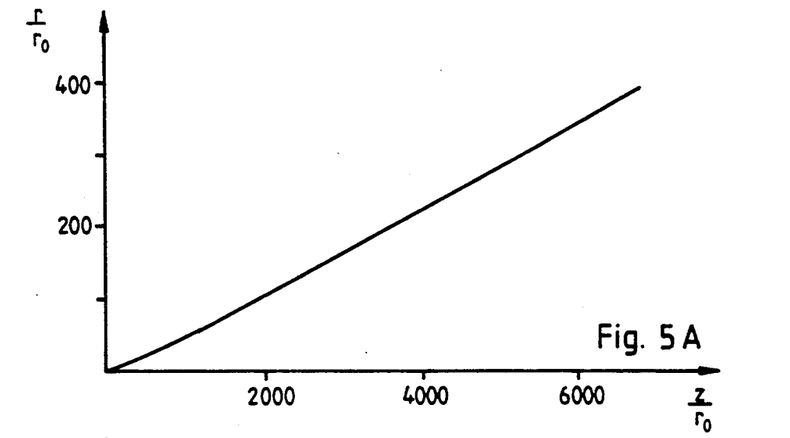
FIG. 5A: Space charge expansion for a 1 ampere 130 keV electron beam at large distances.
Figure 5B:
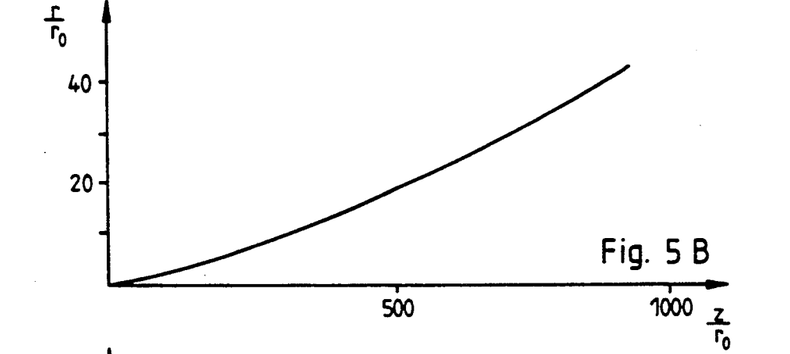
FIG. 5B: Space charge expansion for a 1 ampere 130 keV electron beam at intermediate distances.
Figure 5C:
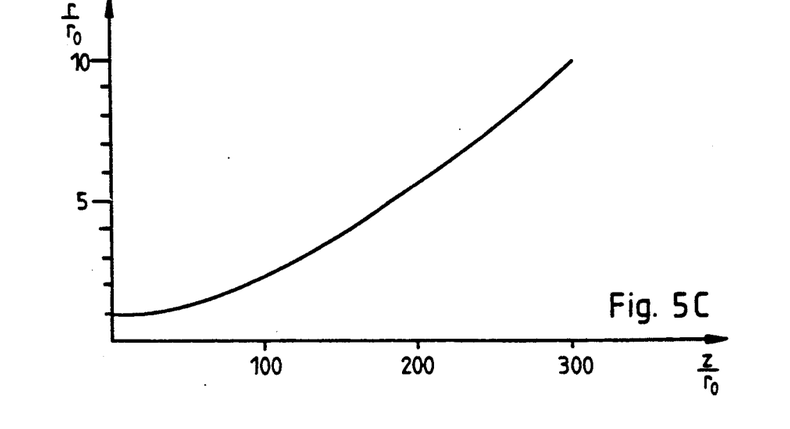
FIG. 5C: Space charge expansion for a 1 ampere 130 keV electron beam at small distances.

FIG. 5A through 5C show the relationship between the beam radius versus distance for a uniform 1 ampere parallel beam of 130 keV electrons in vacuum according to equation 1, i.e. $\epsilon = f = g = 0$, for large (FIG. 5A), intermediate (FIG. 5B), and small (FIG. 5C) values of the reduced variables plotted. The vertical axis variable is the radius of the electron beam in units of the initial radius and the horizontal axis variable the longitudinal distance traveled by electrons in the beam in units of the initial radius. For example, as can be read from FIG. 5C, the beam expands to twice its initial radius after traveling a distance of roughly 100 times its initial radius, i.e. a 0.5 mm radius beam expands to 1.0 mm in radius after traveling a distance of 50 mm. It turns out, for this simplified example, that the distance traveled for a given radial expansion scales with the inverse square root of the beam current and therefore, by way of example, a 0.5 mm radius beam of 100 milliamperes of current expands to 1.0 mm radius after traveling a distance of roughly $50\sqrt{10} \approx 160$ mm.

Figure 6A:
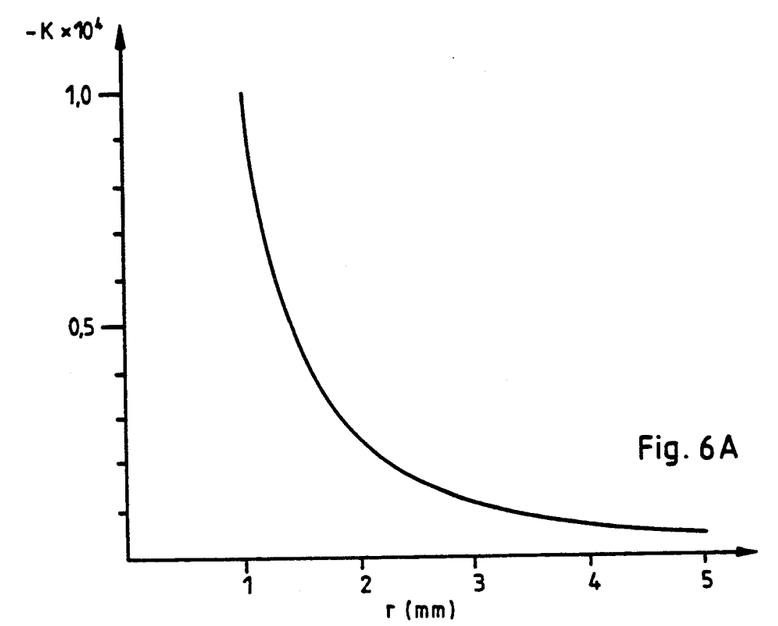
FIG. 6A: Relationship between the generalized beam perveance and the equilibrium beam radius.
Figure 6B:
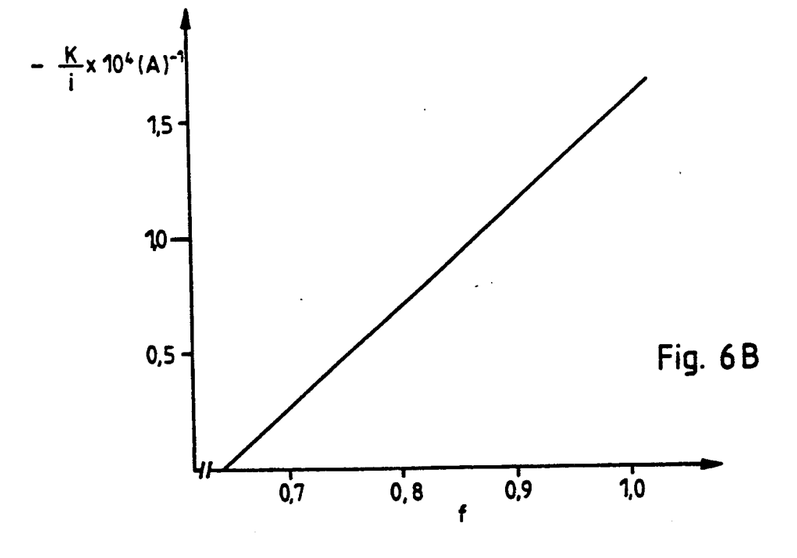
FIG. 6B: Relationship among the generalized beam perveance, the beam current, and the neutralization fraction of the beam.

FIGS. 6A and 6B contrast the behaviour illustrated in FIGS. 5A through 5C with an example of the behaviour when ion aided focussing is used under the approximation that the multiple scattering term is negligible, i.e. $g=0$. As can be seen from equation 1, an equilibrium beam radius can be approximated by the condition $r''=0$, i.e. $K=-\epsilon^2/r^2$. Taking, by way of example, a beam emittance of $10\pi$ mm-mr, the numerical relationships graphed in FIG. 6A result. For example, an equilibrium beam radius of 1 mm requires a perveance of $K=-1 \times 10^{-4}$.

FIG. 6B shows the relationship between the neutralization fraction f and the perveance K in units of the beam current in amperes for a 130 keV electron beam. For example, for an electron beam current of 1 ampere, a K value of $-1 \times 10^{-4}$ requires a neutralization fraction of approximately 87%. In this case, such neutralization fractions can be achieved using partial vacuum pressures of approximately $5.5 \times 10^{-6}$ Torr.( See for example Lee and Cooper, U.S. Pat. No. 4,521,901 and the references contained therein.)

Figure 7A:
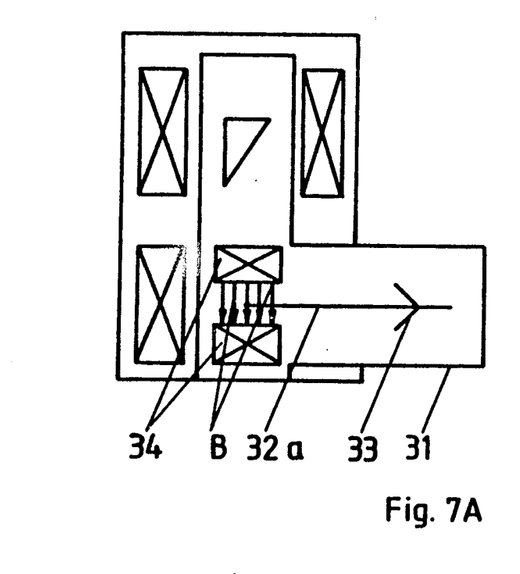
FIG. 7A: Side view of possible scheme for electron beam injection exhibiting a magnetic field.
Figure 7B:
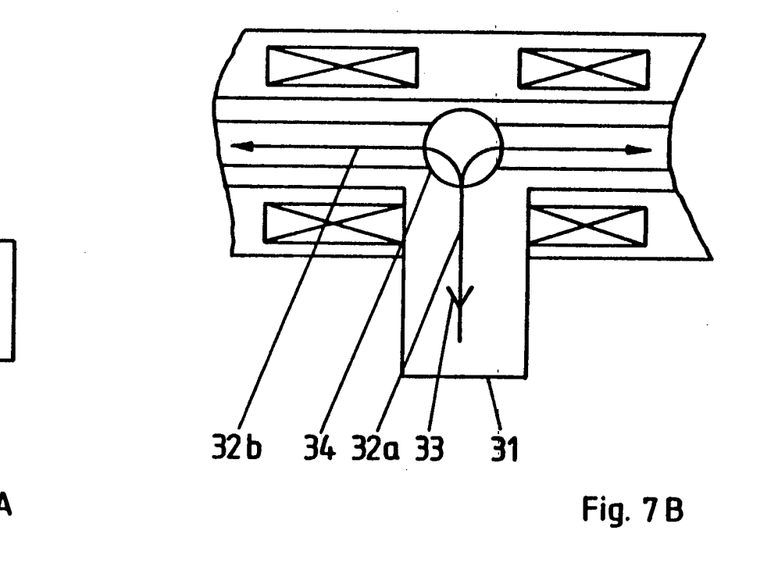
FIG. 7B: Top view of possible scheme for electron beam injection, exhibiting a magnetic field.
Figure 8A:
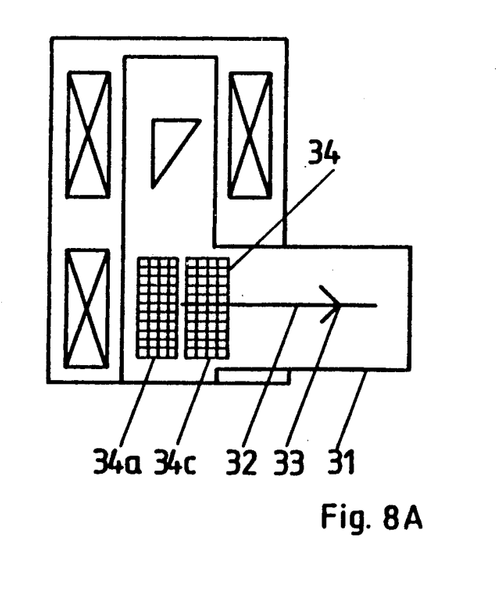
FIG. 8A: Side view of possible scheme for electron beam injection exhibiting an electric field.
Figure 8B:
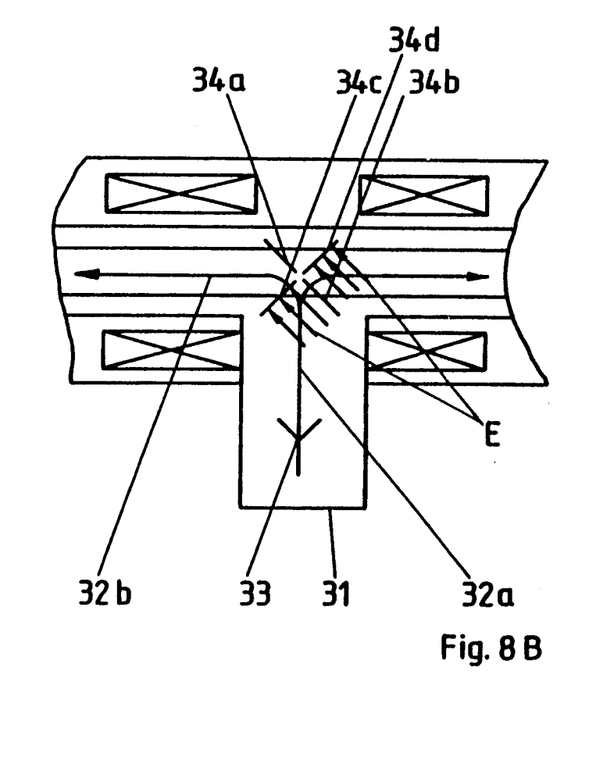
FIG. 8B: Top view of possible scheme for electron beam injection exhibiting an electric field.
Figure 9A:
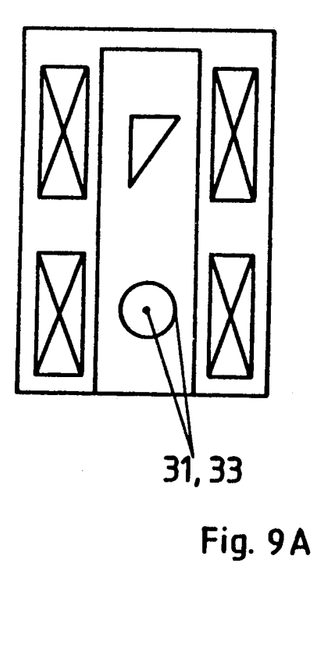
FIG. 9A: Side view of possible scheme for electron beam injection in which the electron beam source is positioned along the orbit of the electron beam.
Figure 9B:
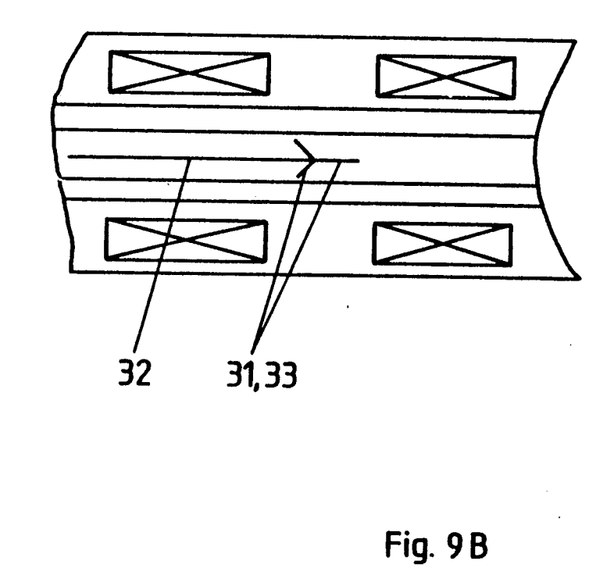
FIG. 9B: Top view of possible scheme for electron beam injection in which the electron beam source is positioned along the orbit of the electron beam.

FIGS. 7A through 9B illustrate various means for electron beam injection. FIGS. 7A, 8A and 9A schematically show side views of a cut through the gantry analogous to that in the top portion of FIG. 1. and FIGS. 7B, 8B, and 9B, a top view. For the sake of clarity, only elements relevant to the electron beam injection are labeled in the figures. In FIGS. 7A through 8B, the electron beam source (31) injects the electron beam over a short distance in a direction largely perpendicular to the scan plane, before bending it in a direction from which it can begin its orbit around the gantry. In FIGS. 9A and 9B, the electron beam source (31) is located aligned along the direction of propagation of the circulating electron beam.

In FIGS. 7A and 7B, injection means (34) exhibit a magnetic field B indicated by the array of vertical arrows in FIG. 7A. As the injecting electron beam (32a) enters into the magnetic field B, it is caused to bend in such a way that it becomes aligned with the direction of the circulating electron beam (32b) and begins its orbit about the gantry. By changing the polarity of the magnetic field B, the electron beam (32) can be caused to orbit in a clockwise or counter-clockwise direction as indicated by the oppositely directed arrows at the ends of the lines representing the circulating electron beam (32b) in FIG. 7B.

FIGS. 8A and 8B show an injection geometry similar to that of FIGS. 7A and 7B, however with the injection means (34) exhibiting electric fields E represented by the slanted array of arrows in FIG. 8B. By applying a sufficiently high negative high voltage to injection means (34), the injecting electron beam (32a) can be deflected into the proper orientation for orbiting as indicated by the lines representing the circulating electron beam (32b). By way of example, by applying a negative high voltage to the portions of the injection means labeled (34c) and (34d), an electric field E (qualitatively represented by the arrows in FIG. 8B) can be generated which will deflect the injecting electron beam (32a) to the "right" in the figure. Correspondingly, low voltage values on injection means (34c) and (34d) and high negative voltages on injection means (34a) and (34b) will cause the injecting electron beam (32a) to be deflected to the "left". Clearly, in this manner, the electron beam can be caused to orbit either clockwise or counterclockwise about the gantry depending on the voltages and associated electric fields of injection means (34a-d). Various values of the electric fields associated with injection means (34a-d) can be selected in order to steer and focus the electron beam (32) and the injection means (34a-d) can exhibit highly transmitting wire mesh to allow the electron beam (32) to pass through when so desired.

FIGS. 9A and 9B illustrate a configuration for the electron beam source (31) in which the injection means (34) are either eliminated or greatly simplified in that the electron beam source (31) is positioned along the orbit of the electron beam (32) so that the electron beam (32) emerging from the electron beam source (31) is injected directly into the orbiting path.

Figure 10:
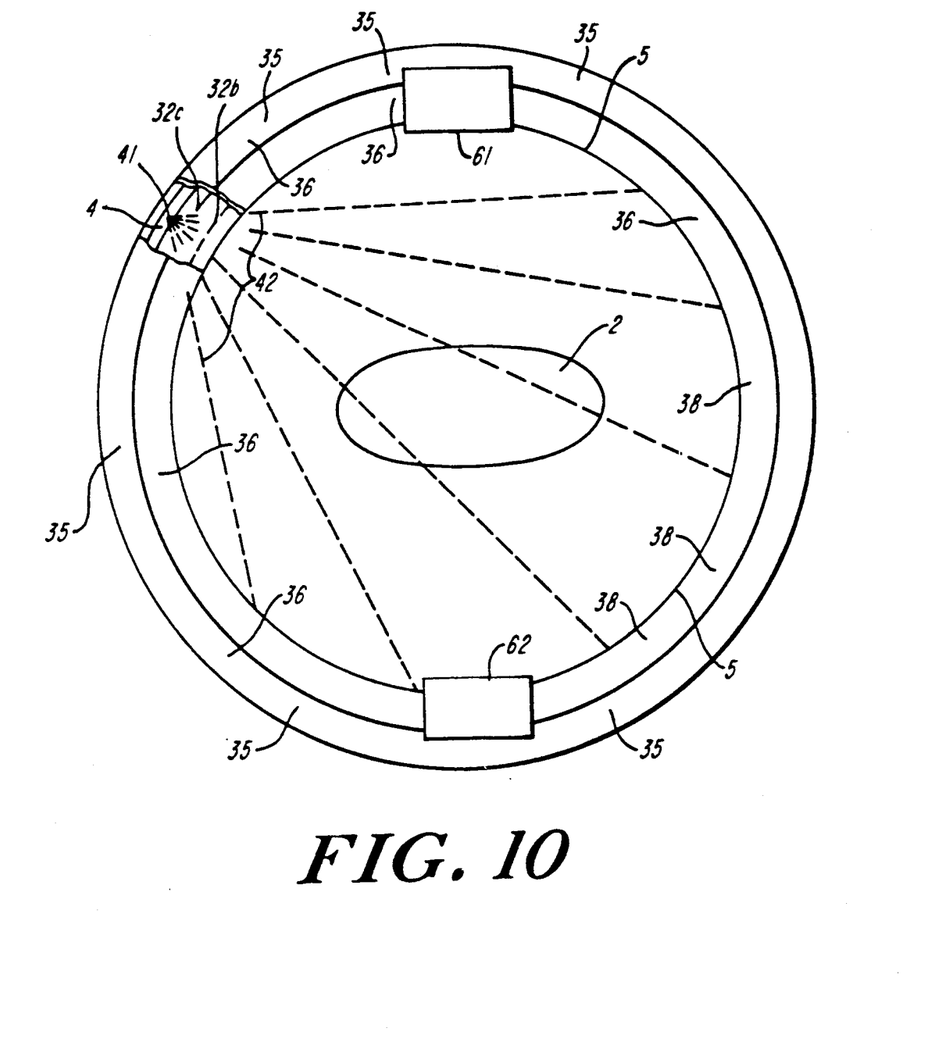
FIG. 10 is a schematic front view of the scanner illustrating a configuration similar to that shown in FIG. 2 but including plural electron sources to generate the orbiting electron beam.

FIG. 10 shows a front view of another preferred embodiment of the invention which utilizes plural electron beam sources (61) and (62). Sources (61) and (62) introduce electrons into the circulating electron beam region (32b) in the same manner as single electron source (31) and may each be constructed in the same manner as single source (31). Although only two electron sources are shown in FIG. 10, additional sources may also be used. The use of plural electron sources such as shown in FIG. 10 has the advantage that the maximum distance which the electron beam produced by each source must travel is reduced to the path length between sources. A reduced beam path length diminishes wellknown problems associated with electron beam divergence and focussing which progressively degrade the beam.

We claim:

1. An x-ray computer tomography system for generating an image of an object, the system comprising:
    a stationary, planar anode ring positioned around the object, the anode ring having a radius;
    an electron beam source for generating an electron beam, said electron beam source being constructed and arranged to generate the electron beam in a direction substantially perpendicular to the planar anode;
    means for deflecting the electron beam into a path which is substantially parallel to the planar anode;
    means for guiding the deflected electron beam in a circulating electron beam path, the path lying in a plane substantially parallel to the anode ring plane and having a radius less than the anode ring radius;
    means for deflecting electrons out of the circular path so that the deflected electrons strike the anode to generate x-ray radiation;
    means for detecting the x-ray radiation which has passed through the object; and
    means responsive to the detected x-ray radiation for generating the image.

2. An x-ray computer tomography system according to claim 1 further comprising an x-ray detector having an arcuate shape and lying in a plane with a radius less than the anode ring radius and being arranged coaxially with respect to the anode ring, the x-ray detector arc extending at least partially around the object.

3. An x-ray computer tomography system according to claim 2, wherein the x-ray detector arc extends completely around the object to form a ring and the x-ray detector ring and the anode ring are substantially coplanar.

4. An x-ray computer tomography system according to claim 3 wherein the x-ray detector ring is comprised of two partial detector rings of substantially equal radius which are positioned parallel to each other and separated by a gap, the gap being large enough to allow x-rays emerging from the focal spot on the anode ring to pass through the gap and the gap being small enough to detect a substantial fraction of x-rays transmitted through the object.

5. In an electron beam x-ray computer tomography system for generating an image of an object, the system having an electron beam source means, an electron beam guiding means, with a stationary anode ring located substantially within a plane, wherein electrons generated by the electron beam source means form an electron beam and the electron beam guiding mean guides the electron beam along a circulating electron beam path located in a plane which is substantially parallel to the plane of the anode ring, and means for deflecting the electron beam out of the circulating electron beam path to collide with the anode ring at a focal spot to emit x-ray radiation, the improvement comprising means located between the electron beam source means and the circulating electron beam path for generating a linear injecting electron beam positioned substantially perpendicular to the plane of the circulating electron beam path, and means for deflecting the injecting electron beam into the circulating electron beam path.

6. In an electron beam x-ray computer tomography system the improvement according to claim 5 wherein the electron beam source means comprises a single electron gun for the generation of the electron beam.

7. In an electron beam x-ray computer tomography system the improvement according to claim 5 wherein the electron beam source means comprises a plurality of separate electron beam sources spaced at intervals around the circular electron beam path.

8. In an electron beam x-ray computer tomography system the improvement according to claim 5 wherein the electron beam guiding means comprises beam steering means for bending the electron beam path, and means for focussing the electron beam along the circulating electron beam path by means of ion aided focussing.

9. In an electron beam x-ray computer tomography system the improvement according to claim 5 wherein the deflecting means comprises means for selectively bending the injecting electron beam in a first direction and a second direction opposite to the first direction whereby the electron beam travels in a clockwise and a counter-clockwise orbit around the object being scanned.

10. In an electron beam x-ray computer tomography system the improvement according to claim 5 wherein the deflecting means comprises means for generating an electromagnetic field which electromagnetic field selectively bends the injecting electron beam in a first direction and in a second direction opposite to the first direction.

11. In an electron beam x-ray computer tomography system the improvement according to claim 5 wherein the deflecting means comprises means for generating an electrostatic field which electrostatic field selectively bends the injecting electron beam in a first direction and a second direction opposite to the first direction.

12. In an electron beam x-ray computer tomography system for generating an image of an object, the system having an electron beam source, an electron beam guiding means, a stationary planar anode ring having a radius, an x-ray detector ring having a radius less than the anode ring radius and being arranged coaxially with respect to the anode ring wherein the electrons generated by the electron beam source are guided by the guiding means along a circulating electron beam path which lies in a plane substantially parallel to the plane of the anode ring and has a path radius larger than the x-ray detector ring radius and smaller than the anode ring radius and means for causing the electrons to collide with the anode ring at a focal spot to emit x-ray radiation, the improvement comprising beam forming means for generating a linear injecting electron beam positioned substantially perpendicular to the electron beam path and intersecting the electron beam path, and means for deflecting the injecting electron beam through an angle of substantially 90° so that the injecting electron beam is tangential to the circulating electron beam path.

13. In an electron beam x-ray computer tomography system the improvement according to claim 12 wherein the electron beam guiding means comprises means for focussing the electron beam by means of ion aided focussing.

14. In an electron beam x-ray computer tomography system the improvement according to claim 12 wherein the deflecting means comprises means for selectively bending the injecting electron beam substantially 90° in a first direction and substantially 90° in a second direction opposite to the first direction whereby the electron beam is guided in a clockwise and a counter-clockwise orbit around the object being scanned.

15. In an electron beam x-ray computer tomography system for generating an image of an object, the system having a stationary anode with an elongated contour that lies substantially within a plane and at least partially surrounds the object, an electron beam source generating an electron beam, means for bending the electron beam into a circulating electron beam part which follows the anode contour means for positioning the circulating electron beam part substantially within a plane which is parallel to the plane of the anode contour, and means for deflecting the circulating electron beam part so that the circulating electron beam part strikes the anode contour at a selected spot, the improvement wherein the electron beam source produces an injecting electron beam part which is substantially perpendicularly to the circulating electron beam part, and wherein the electron beam positioning means comprises a deflector located between the electron beam source and the circulating electron beam part which deflector bends the injecting electron beam part so that it becomes the circulating electron beam part.

16. In an electron beam x-ray computer tomography system the improvement according to claim 15 wherein the deflector comprises means for selectively bending the injecting electron beam part in a first direction and a second direction opposite to the first direction whereby the electron beam can be controlled to travel in a clockwise and a counter-clockwise orbit around the object being scanned.

* * * * *